(12) United States Patent
Harmouche

(10) Patent No.: US 11,596,776 B2
(45) Date of Patent: Mar. 7, 2023

(54) FLUID CONTAINER REPLACEMENT SYSTEM AND METHOD

(71) Applicant: Boston Scientific Scimed Inc., Maple Grove, MN (US)

(72) Inventor: Chadi Harmouche, Saint-Laurent (CA)

(73) Assignee: Boston Scientific Scimed, Inc., Maple Grove, MN (US)

( * ) Notice: Subject to any disclaimer, the term of this patent is extended or adjusted under 35 U.S.C. 154(b) by 764 days.

(21) Appl. No.: 16/576,038

(22) Filed: Sep. 19, 2019

(65) Prior Publication Data
US 2020/0009358 A1    Jan. 9, 2020

Related U.S. Application Data

(63) Continuation of application No. PCT/US2018/021090, filed on Mar. 6, 2018.
(Continued)

(51) Int. Cl.
*A61B 18/02* (2006.01)
*A61M 25/10* (2013.01)
(Continued)

(52) U.S. Cl.
CPC ....... *A61M 25/10185* (2013.11); *A61B 18/02* (2013.01); *A61B 2018/0022* (2013.01);
(Continued)

(58) Field of Classification Search
CPC ............ A61B 18/02; A61B 2018/0022; A61B 2018/00642; A61B 2018/00666;
(Continued)

(56) References Cited

U.S. PATENT DOCUMENTS 5,477,690 A    12/1995    Gram
9,074,921 B1    7/2015    Parker et al.
(Continued)

FOREIGN PATENT DOCUMENTS

CN    105299462 A    2/2016

OTHER PUBLICATIONS

"Replacing the Waste Toner Container" (CANON) May 24, 2016, Retrieved from the Internet on May 17, 2018.
(Continued)

*Primary Examiner* — Michael F Peffley
(74) *Attorney, Agent, or Firm* — Nelson Mullins Riley & Scarborough LLP

(57) ABSTRACT

A container replacement system for replacing a fluid container with a replacement fluid container, wherein the fluid container contains a cryogenic fluid and is coupled to a pressure line, includes a control valve that vents the cryogenic fluid within the pressure line, a pressure sensor that senses a line pressure of the cryogenic fluid and generates sensor output and a controller that receives sensor output and determines whether to replace the fluid container. If the line pressure is below a threshold line pressure, the controller determines replacing the fluid container is permissible. Contrarily, if the line pressure is above the threshold line pressure, the controller determines replacing the fluid container is not permissible. The container replacement system further includes a GUI that instructs whether replacing the fluid container is permissible.

14 Claims, 8 Drawing Sheets

Related U.S. Application Data

(60) Provisional application No. 62/509,974, filed on May 23, 2017, provisional application No. 62/474,402, filed on Mar. 21, 2017.

(51) Int. Cl.
*A61B 18/00* (2006.01)
*A61B 34/00* (2016.01)

(52) U.S. Cl.
CPC ............... *A61B 2018/00666* (2013.01); *A61B 2018/0212* (2013.01); *A61B 2018/0262* (2013.01); *A61B 2034/252* (2016.02); *A61M 2025/1043* (2013.01); *A61M 2202/03* (2013.01); *A61M 2205/3334* (2013.01)

(58) Field of Classification Search
CPC .. A61B 2018/00863; A61B 2018/0212; A61B 2018/0262; A61B 2034/252; A61B 2090/064; A61M 2025/1043; A61M 2202/03; A61M 2205/3334; A61M 25/10185
See application file for complete search history.

(56) References Cited

U.S. PATENT DOCUMENTS

| | | | |
|---|---|---|---|
| 9,089,316 B2* | 7/2015 | Baust | A61B 18/02 |
| 10,788,244 B2* | 9/2020 | Mahrouche | F25B 45/00 |
| 2003/0018326 A1* | 1/2003 | Abboud | A61B 18/02 606/20 |
| 2007/0032783 A1 | 2/2007 | Abboud et al. | |
| 2013/0231651 A1 | 9/2013 | Burr et al. | |
| 2014/0116402 A1 | 5/2014 | Horiba et al. | |
| 2014/0276698 A1* | 9/2014 | Wittenberger | A61B 18/02 606/21 |
| 2015/0351822 A1 | 12/2015 | Mulcahey et al. | |
| 2016/0008049 A1* | 1/2016 | Mahrouche | A61B 18/02 606/21 |

OTHER PUBLICATIONS

International Search Report and Written Opinion received for PCT Patent Application No. PCT/US2018/021090, dated Jun. 27, 2018, 20 pages.
Measuring liquid level in a sealed tank with a hydrostatic pressure sensor (SENSORSONE) Nov. 5, 2016, Retrieved from the Internet on May 15, 2018.

* cited by examiner

FLUID CONTAINER REPLACEMENT SYSTEM AND METHOD

CROSS-REFERENCE TO RELATED APPLICATION

This application is a continuation of International Application No. PCT/US2018/021090, with an international filing date of Mar. 6, 2018, which claims the benefit of U.S. Provisional Application No. 62/474,403 filed on Mar. 21, 2017 and entitled "FLUID CONTAINER REPLACEMENT SYSTEM AND METHOD"; and U.S. Provisional Application Ser. No. 62/509,974 filed on May 23, 2017 and entitled "FLUID MEASUREMENT SYSTEM AND METHOD". As far as permitted, the contents of International Application No. PCT/US2018/21090 and U.S. Provisional Application Ser. Nos. 62/474,403 and 62/509,974 are incorporated in their entirety herein by reference.

TECHNICAL FIELD

The present invention relates to medical devices and methods for cryoablation. More specifically, the invention relates to devices and methods for delivering cryogenic fluid to a cryoablation system fluid source.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few. In particular, catheter ablation involves delivering ablative energy to tissue inside the heart to block aberrant electrical activity from depolarizing heart muscle cells out of synchrony with the heart's normal conduction pattern. The procedure is performed by positioning the tip of an energy delivery catheter adjacent to diseased or targeted tissue in the heart. The energy delivery component of the system is typically at or near the most distal (i.e. farthest from the operator or user) portion of the catheter, and often at the tip of the catheter.

Various forms of energy can be used to ablate diseased heart tissue. One form of energy that is used to ablate diseased heart tissue includes cryogenics (also referred to herein as "cryoablation"). During a cryoablation procedure, the tip of the catheter is positioned adjacent to targeted cardiac tissue, at which time energy is delivered in the form of a refrigerant or cryogenic fluid to create tissue necrosis, rendering the ablated tissue incapable of conducting electrical signals.

Cryosurgical, and in particular, catheter-based cryoablation systems consume various cryogenic fluids (e.g., liquid nitrous oxide or liquid nitrogen) that are typically provided in high-pressure fluid containers in either liquid or gas form (collectively referred to herein as "cryogenic fluid"). During cryoablation procedures, one or more alternative fluid containers may be used to contain the cryogenic fluid. In various applications, fluid containers of multiple sizes and designs may be used, leading to potentially broad ranges of capacities and weights. The wide-ranging capacities and weights can make it difficult to accurately assess whether there is a sufficient quantity of cryogenic fluid contained within the fluid container to successfully complete the cryoablation procedure. However, it is appreciated that these fluid containers should have sufficient cryogenic fluid therein in order to successfully complete such procedures. Complete depletion of the cryogenic fluid during the cryoablation procedure would not only interrupt the procedure, but it could also be injurious to the patient. Accordingly, it is desired to be able to accurately assess the amount of cryogenic fluid that is present within the fluid container at any given time.

Additionally, when the level of cryogenic fluid within the fluid container is determined to be below a certain predetermined level, it is understood that such fluid container needs to be replaced, i.e. needs to be removed and replaced with a replacement high-pressure fluid container that has sufficient cryogenic fluid to successfully complete the desired procedures. When replacing the fluid container, in some instances, an operator or user may neglect to completely or properly close the fluid container or may otherwise close the fluid container insufficiently, and thereby release high-pressure cryogenic fluid which can cause injury to the operator or user. Accordingly, it is desired to provide a system that assists the operator or user in inhibiting the potential release of the high-pressure cryogenic fluid during replacement or exchange of fluid containers.

SUMMARY

The present invention is directed toward a fluid container replacement system (also sometimes referred to as a "container replacement system") for replacing a fluid container with a replacement fluid container. The fluid container can be coupled to a pressure line. In various embodiments, the container replacement system includes a control valve, a pressure sensor and a controller. The control valve can vent a cryogenic fluid within the pressure line. The pressure sensor can sense a line pressure of any cryogenic fluid within the pressure line and generate sensor output. The controller can receive the sensor output and determine whether to replace the fluid container with the replacement fluid container based at least partially on the sensor output.

In certain embodiments, the control valve can be manually controlled. In other embodiments, the control valve can be controlled by the container replacement system, via the controller.

In some embodiments, the pressure sensor can sense the line pressure of the cryogenic fluid within the pressure line after the control valve has vented the cryogenic fluid within the pressure line.

Additionally, in one embodiment, the controller can compare the line pressure of the cryogenic fluid within the pressure line to a threshold line pressure. If the line pressure of the cryogenic fluid within the pressure line is below the threshold line pressure, then the controller can determine that replacing the fluid container with the replacement fluid container is permissible. Conversely, if the line pressure of the cryogenic fluid within the pressure line is above the threshold line pressure, then the controller can determine that replacing the fluid container with the replacement fluid container is not permissible.

In various embodiments, the container replacement system can further include a graphical user interface. The graphical user interface can instruct whether replacing the fluid container with the replacement fluid container is permissible. In one embodiment, the graphical user interface can instruct to replace the fluid container with the replacement fluid container. In another embodiment, the graphical user interface can instruct to close the fluid container.

Alternatively, the graphical user interface can provide a set of instructions for replacing the fluid container with the replacement fluid container.

The present invention is also directed toward a cryogenic balloon catheter system (also sometimes referred to as a "catheter system") including a balloon catheter, a fluid container with a cryogenic fluid that is selectively directed into the balloon catheter, and a container replacement system for replacing the fluid container with a replacement fluid container.

Additionally, the present invention is also directed toward a method for replacing a fluid container with a replacement fluid container. The method can include the steps of venting with a control valve a cryogenic fluid within the pressure line, generating sensor output with a pressure sensor, sending the sensor output to a controller and determining with the controller whether to replace the fluid container with the replacement fluid container based at least partially on the sensor output.

In certain embodiments, the step of venting can be manually controlled. In other embodiments, the step of venting can be controlled via the controller.

In some embodiments, the step of generating can further include sensing with the pressure sensor a line pressure of the cryogenic fluid within the pressure line after the control valve has vented the cryogenic fluid within the pressure line.

Further, in one embodiment, the step of determining can include comparing the line pressure of the cryogenic fluid within the pressure line to a threshold line pressure. The step of determining can further include determining that replacing the fluid container with the replacement fluid container is permissible if the line pressure of the cryogenic fluid within the pressure line is below a threshold line pressure. Contrarily, the step of determining can also include determining that replacing the fluid container with the replacement fluid container is not permissible if the line pressure of the cryogenic fluid within the pressure line is above the threshold line pressure.

In certain embodiments, the method can further include the step of instructing with a graphical user interface whether replacing the fluid container with the replacement fluid container is permissible. In one embodiment, the step of instructing includes instructing to replace the fluid container with the replacement fluid container. Alternatively, the step of instructing can include instructing to close the fluid container. In other embodiments, the step of instructing can include providing a set of instructions for replacing the fluid container with the replacement fluid container.

Further, in some applications, the present invention is directed toward a container replacement system for replacing a fluid container with a replacement fluid container, the fluid container being coupled to a pressure line, the container replacement system including a control valve that vents the cryogenic fluid within the pressure line; a pressure sensor that senses a line pressure of the cryogenic fluid within the pressure line; a controller that receives the line pressure, the controller comparing the line pressure of the cryogenic fluid within the pressure line to a threshold line pressure, wherein if the line pressure of the cryogenic fluid within the pressure line is below the threshold line pressure, then the controller determines replacing the fluid container with the replacement fluid container is permissible; and a graphical user interface that instructs whether replacing the fluid container with the replacement fluid container is permissible.

The present invention is directed toward a fluid container measurement system (also sometimes referred to as a "container measurement system") for determining a fluid quantity of a cryogenic fluid within a fluid container. In various embodiments, the container measurement system includes a container scale and a controller. The container scale can weigh the fluid container and the cryogenic fluid within the fluid container to obtain container weight information. The controller can receive the container weight information and determine the fluid quantity of the cryogenic fluid within the fluid container based at least partially on the container weight information.

In certain embodiments, the container measurement system can include a container sensor. The container sensor can sense dimensions of the fluid container to obtain container dimension information. In various embodiments, the controller can receive the container dimension information to determine the fluid quantity of the cryogenic fluid within the fluid container based at least partially on at least one of the container dimension information and the container weight information.

In certain embodiments, the fluid container can include a tare weight. The controller can receive the container weight information and the container dimension information and determine the tare weight of the fluid container based at least partially on at least one of the container weight information and the container dimension information.

In various embodiments, the fluid container can include identification information. In such embodiments, the container sensor can sense the identification information of the fluid container to obtain the tare weight of the fluid container.

In some embodiments, the controller can determine the fluid quantity of the fluid container based at least partially on the tare weight of the fluid container.

In certain embodiments, the container measurement system can further include a graphical user interface that displays the fluid quantity of the cryogenic fluid within the fluid container.

Further, in certain applications, the present invention is directed toward a container measurement system for determining a fluid quantity of a cryogenic fluid within a fluid container. The fluid container can include at least one of container dimension information and identification information. In various embodiments, the container measurement system can include a container scale that can weigh the fluid container and the cryogenic fluid within the fluid container to obtain container weight information, a graphical user interface that is configured to manually receive input from the operator of at least one of the container dimension information and the identification information and a controller that can receive the container weight information and at least one of the container dimension information and the identification information and determine the fluid quantity of the cryogenic fluid within the fluid container based at least partially on the container weight information.

In some embodiments, the fluid container can include a tare weight. In such embodiments, the graphical user interface is configured to manually receive input of the tare weight of the fluid container and the controller can receive the tare weight of the fluid container. In certain embodiments, the controller can determine the fluid quantity of the cryogenic fluid within the fluid container based at least partially on the tare weight of the fluid container.

The present invention is also directed toward a method for determining a fluid quantity of a cryogenic fluid within a fluid container. The method can include the steps of weighing with a container scale the fluid container that contains the cryogenic fluid to obtain container weight information, sending the container weight information from the container scale to a controller and determining with a controller the fluid quantity of the cryogenic fluid within the fluid container based at least partially on the container weight information.

In certain embodiments, the method can further include the step of sensing with a container sensor dimensions of the fluid container to obtain container dimension information and the step of sending the container dimension information to the controller. In these embodiments, the step of determining can include determining the fluid quantity of the cryogenic fluid within the fluid container based at least partially on at least one of the container weight information and the container dimension information.

Further, in some embodiments, the step of sensing can include sensing with a container sensor identification information of the fluid container to obtain a tare weight of the fluid container and sending the identification information to the controller. In such embodiments, the step of determining can include determining the fluid quantity of the cryogenic fluid within the fluid container based at least partially on the tare weight of the fluid container.

Additionally, the present invention is direct toward a method for determining a fluid quantity of a cryogenic fluid within a fluid container, the method including the steps of weighing with a container scale the fluid container that contains the cryogenic fluid to obtain container weight information; manually inputting with a graphical user interface at least one of container dimension information, identification information and a tare weight of the fluid container; sending the container weight information and at least one of the container dimension information, the identification information and the tare weight of the fluid container to a controller; and determining with the controller the fluid quantity of the cryogenic fluid within the fluid container based at least partially on the container weight information and at least one of the container dimension information, the identification information and the tare weight of the fluid container.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION

Embodiments of the present invention are described herein in the context of a fluid container measurement system (also sometimes referred to as a "container measurement system") and a fluid container replacement system (also sometimes referred to as a "container replacement system"), and corresponding methods, which are usable with a suitable ablation system and/or catheter system. In particular, as provided in detail herein, the container measurement system can include various features that enable an operator or user to more accurately assess the level of cryogenic fluid within a fluid container at any given time. Additionally, the container replacement system can provide detailed instructions to the operator or user to ensure that when replacement of the fluid container is deemed necessary, the replacement can be done in a more safe, convenient and effective manner.

Those of ordinary skill in the art will realize that the following detailed description of the present invention is illustrative only and is not intended to be in any way limiting. Other embodiments of the container measurement system and container replacement system will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1:
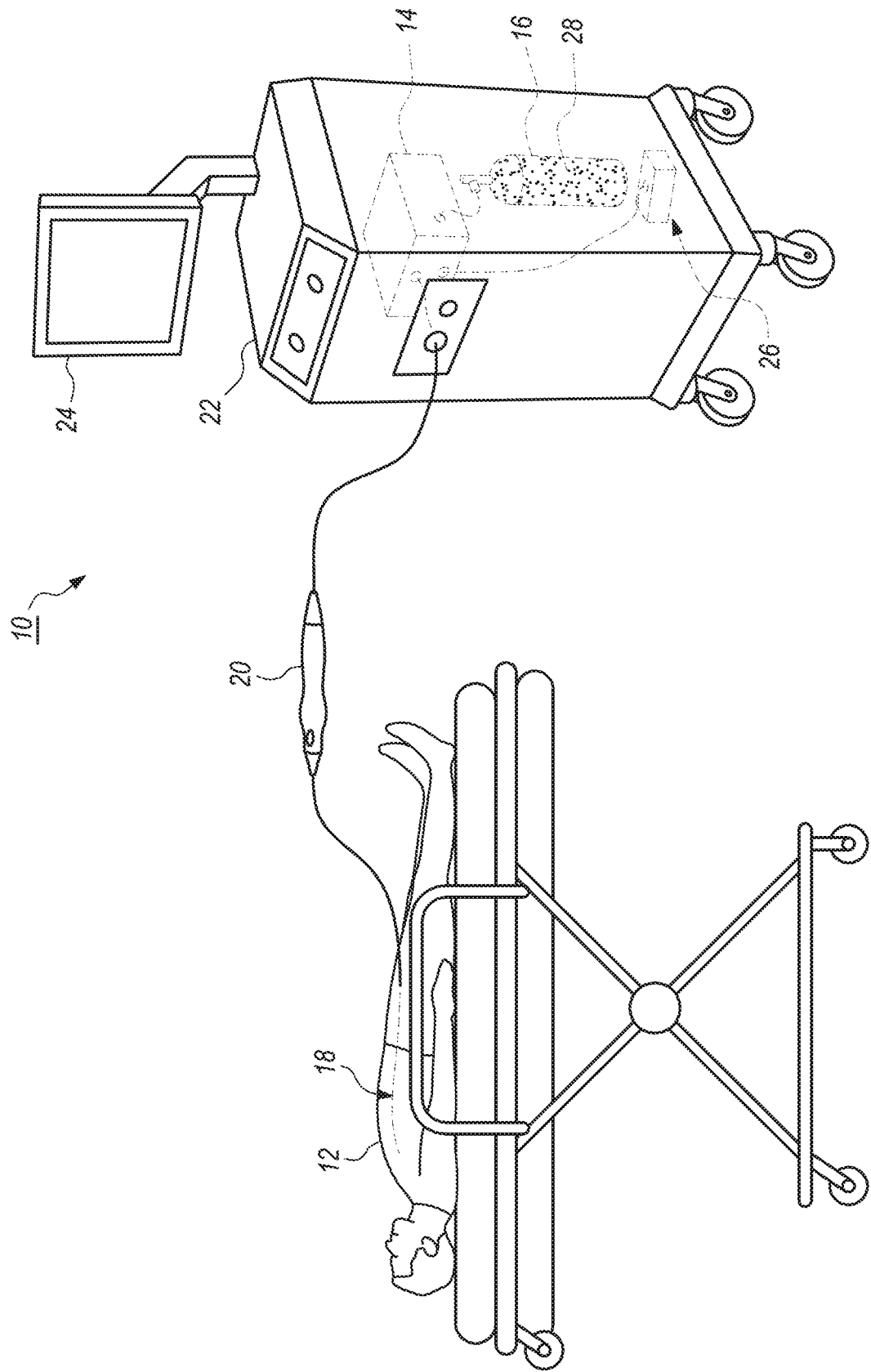
FIG. 1 is a schematic view of a patient, and one embodiment of a cryogenic balloon catheter system including a fluid container measurement system having features of the present invention.

FIG. 1 is a schematic view of one embodiment of a cryogenic balloon catheter system 10 (also sometimes referred to as a "catheter system") for use with a patient 12, which can be a human being or an animal. Although the catheter system 10 is specifically described herein with respect to the cryogenic balloon catheter system, it is understood and appreciated that other types of catheter systems and/or ablation systems can equally benefit by the teachings provided herein. For example, in certain non-exclusive alternative embodiments, the present invention can be equally applicable for use with any suitable types of ablation systems and/or any suitable types of catheter systems. Thus, the specific reference herein to use as part of the cryogenic balloon catheter system is not intended to be limiting in any manner.

The design of the catheter system 10 can be varied. In certain embodiments, such as the embodiment illustrated in FIG. 1, the catheter system 10 can include one or more of a control system 14, a fluid source 16 (e.g., one or more fluid containers), a balloon catheter 18, a handle assembly 20, a control console 22, a graphical display 24 (also sometimes referred to as a graphical user interface or "GUI") and a container measurement system 26. It is understood that although FIG. 1 illustrates the structures of the catheter system 10 in a particular position, sequence and/or order, these structures can be located in any suitably different position, sequence and/or order than that illustrated in FIG. 1. It is also understood that the catheter system 10 can include fewer or additional components than those specifically illustrated and described herein.

In various embodiments, the control system 14 is configured to monitor and control the various processes of the ablation procedure. More specifically, the control system 14 can monitor and control release and/or retrieval of a cryogenic fluid 28 to and/or from the balloon catheter 18. The control system 14 can also control various structures that are responsible for maintaining and/or adjusting a flow rate and/or pressure of the cryogenic fluid 28 that is released to the balloon catheter 18 during the cryoablation procedure. In such embodiments, the catheter system 10 delivers ablative energy in the form of cryogenic fluid 28 to cardiac tissue of the patient 12 to create tissue necrosis, rendering the ablated tissue incapable of conducting electrical signals. Additionally, in various embodiments, the control system 14 can control activation and/or deactivation of one or more other processes of the balloon catheter 18. Further, or in the alternative, the control system 14 can receive data and/or other information (also sometimes referred to as "sensor output") from various structures within the catheter system 10. In various embodiments, the control system 14 and the GUI 24 and/or the container measurement system 26 can be electrically connected and/or coupled. In some embodiments, the control system 14 can receive, monitor, assimilate and/or integrate any sensor output and/or any other data or information received from any structure within the catheter system 10 in order to control the operation of the balloon catheter 18. Still further, or in the alternative, the control system 14 can control positioning of portions of the balloon catheter 18 within the body of the patient 12, and/or can control any other suitable functions of the balloon catheter 18.

The fluid source 16 (also sometimes referred to as "fluid container 16") can include one or more fluid container(s) 16. It is understood that while one fluid container 16 is illustrated in FIG. 1, any suitable number of fluid containers 16 may be used. The fluid container(s) 16 can be of any suitable size, shape and/or design. The fluid container(s) 16 contains the cryogenic fluid 28, which is delivered to the balloon catheter 18 with or without input from the control system 14 during a cryoablation procedure. Additionally, the type of cryogenic fluid 28 that is used during the cryoablation procedure can vary. In one non-exclusive embodiment, the cryogenic fluid 28 can include liquid nitrous oxide. In another non-exclusive embodiment, the cryogenic fluid 28 can include liquid nitrogen. However, any other suitable cryogenic fluid 28 can be used.

The design of the balloon catheter 18 can be varied to suit the specific design requirements of the catheter system 10. As shown, the balloon catheter 18 is inserted into the body of the patient 12 during the cryoablation procedure. In one embodiment, the balloon catheter 18 can be positioned within the body of the patient 12 using the control system 14. Stated in another manner, the control system 14 can control positioning of the balloon catheter 18 within the body of the patient 12. Alternatively, the balloon catheter 18 can be manually positioned within the body of the patient 12 by a qualified health professional (also referred to herein as an "operator" or "user"). As used herein, health care professional, operator and/or user can include a physician, a physician's assistant, a nurse and/or any other suitable person and/or individual. In certain embodiments, the balloon catheter 18 is positioned within the body of the patient 12 utilizing at least a portion of the sensor output that is received from the balloon catheter 18. For example, in various embodiments, the sensor output is received by the control system 14, which can then provide the operator with information regarding the positioning of the balloon catheter 18. Based at least partially on the sensor output feedback received by the control system 14, the operator can adjust the positioning of the balloon catheter 18 within the body of the patient 12 to ensure that the balloon catheter 18 is properly positioned relative to target cardiac tissue. While specific reference is made herein to the balloon catheter 18, as noted above, it is understood that any suitable type of medical device and/or catheter may be used.

The handle assembly 20 is handled and used by the operator or user to operate, position and control the balloon catheter 18. The design and specific features of the handle assembly 20 can vary to suit the design requirements of the catheter system 10. In the embodiment illustrated in FIG. 1, the handle assembly 20 is separate from, but in electrical and/or fluid communication with the control system 14, the fluid container 16, the graphical display 24 and/or the container measurement system 26. In some embodiments, the handle assembly 20 can integrate and/or include at least a portion of the control system 14 within an interior of the handle assembly 20. It is understood that the handle assembly 20 can include fewer or additional components than those specifically illustrated and described herein.

In the embodiment illustrated in FIG. 1, the control console 22 includes at least a portion of the control system 14, the fluid container 16, the GUI 24 and/or the container measurement system 26. However, in alternative embodiments, the control console 22 can contain additional structures not shown or described herein. Still alternatively, the control console 22 may not include various structures that are illustrated within the control console 22 in FIG. 1. For example, in certain non-exclusive alternative embodiments, the control console 22 does not include the GUI 24.

In various embodiments, the GUI 24 is electrically connected to the control system 14 and/or the container measurement system 26. Additionally, the GUI 24 provides the operator or user of the catheter system 10 with information that can be used before, during and after the cryoablation procedure. For example, the GUI 24 can provide the operator or user with information based on the sensor output, and any other relevant information that can be used before, during and after the cryoablation procedure. The specifics of the GUI 24 can vary depending upon the design requirements of the catheter system 10, or the specific needs, specifications and/or desires of the operator or user.

In one embodiment, the GUI 24 can provide static visual data and/or information to the operator or user. In addition, or in the alternative, the GUI 24 can provide dynamic visual data and/or information to the operator or user, such as video data or any other data that changes over time, e.g., during an ablation procedure. Further, in various embodiments, the GUI 24 can include one or more colors, different sizes, varying brightness, etc., that may act as alerts to the operator or user. Additionally, or in the alternative, the GUI 24 can provide audio data or information to the operator or user.

The container measurement system 26 measures a quantity of the cryogenic fluid 28 within the fluid container(s) 16 (also sometimes referred to as "fluid quantity"), for example, when selecting the fluid container 16 prior to use for the cryoablation procedure. In particular, the container measurement system 26 is specifically configured to provide the operator or user of the catheter system 10 with information to determine whether there is a sufficient fluid quantity within the fluid container 16 to perform the cryoablation procedure. Once the fluid quantity within the fluid container 16 is determined, the fluid container 16 can then be selectively used by the operator or user to provide the cryogenic fluid 28 for use by the catheter system 10 during the cryoablation procedure.

In the embodiment illustrated in FIG. 1, at least a portion of the container measurement system 26 is positioned at a location within the control console 22. The container measurement system 26 can be positioned at any suitable location within the control console 22. Alternatively, the container measurement system 26 can be positioned at any suitable location outside of the control console 22. Further, portions of the container measurement system 26 can be positioned partially within and/or outside the control console 22. Additionally, and/or alternatively, the container measurement system 26 can be positioned at any other suitable location within the catheter system 10. The specific components and operations of the container measurement system 26 will be described in greater detail herein below in relation to the embodiment illustrated in FIG. 2.

Figure 2:
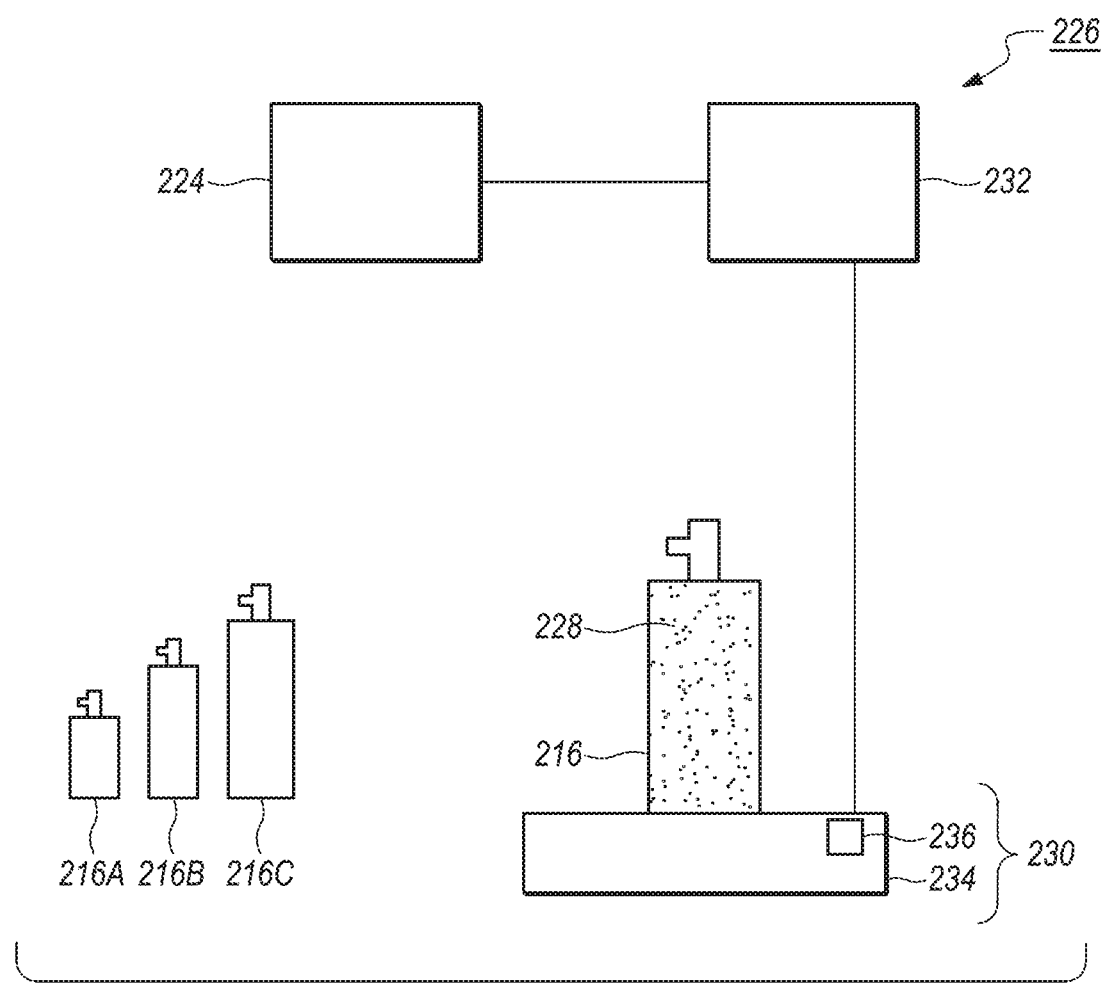
FIG. 2 is a simplified schematic side view of one or more fluid containers that contain the cryogenic fluid and one embodiment of the fluid container measurement system.

FIG. 2 is a simplified schematic side view of one or more fluid containers 216 that contain the cryogenic fluid 228 and one embodiment of the container measurement system 226. The design of the container measurement system 226 can be varied. As shown in this embodiment illustrated in FIG. 2, the container measurement system 226 can include one or more of the GUI 224, a scale assembly 230 and a controller 232. Alternatively, the container measurement system 226 can include additional components or fewer components than those specifically illustrated and described herein.

The container measurement system 226 enables the operator or user to more accurately assess whether there is sufficient fluid quantity within the fluid container 216 to successfully complete the cryoablation procedure. For ease of understanding, three different fluid containers 216A, 216B, 216C, of varying size, shape and/or design, are illustrated in FIG. 2, which are also referred to generically herein as "fluid container 216." In certain embodiments, such as the embodiment illustrated in FIG. 2, the fluid container 216 can include a tare weight and a container capacity. The tare weight includes the weight of the fluid container 216 when the fluid container 216 is empty, e.g., containing no or substantially no cryogenic fluid 228. In various embodiments, the tare weight of the fluid container 216 can be used to determine the fluid quantity, i.e., the amount of cryogenic fluid 228 remaining within the fluid container 216. The container capacity includes the maximum amount, e.g., volume, of cryogenic fluid 228 that may be contained within the fluid container 216. In one embodiment, the container capacity may be expressed in terms of a weight of a maximum volume of cryogenic fluid 228 that may be contained within the fluid container 216. As the size, shape and/or design of the fluid containers 216 can vary, it is understood that the tare weight and the container capacity can also vary. Additionally, and/or alternatively, the fluid container 216 can include any form of container or tank that is configured to contain a gas or a liquid that is often under pressure or otherwise in a compressed form.

In one embodiment, the container measurement system 226 can sense and/or process certain information received about varying dimensions of the fluid container 216, including height, diameter or circumference, as non-exclusive examples (also sometimes referred to as "container dimension information"). Alternatively, the container dimension information can include any other suitable dimensions and/or measurements of the fluid container 216. In another embodiment, the container measurement system 226 can measure and/or process certain information received about a weight of the fluid container 216, which may include the tare weight of the fluid container 216, the weight of the cryogenic fluid 228 therein, or both, as non-exclusive examples (also sometimes referred to as "container weight information"). Alternatively, the container weight information can include any other suitable weight relating to the fluid container 216 and/or the cryogenic fluid 228 therein. Additionally, and/or alternatively, it is understood that the container dimension information and the container weight information of the fluid container 216 can include any other suitable measurements and/or units that can be used to process information about the dimensions and/or weight of the fluid container 216.

The GUI 224 of the container measurement system 226 allows the operator or user to interact with the container measurement system 226 and/or the catheter system 210. In other words, the GUI 224 can allow the operator or user to manually input information into the catheter system 210. As used herein, the term "manually input" can include the use of a touchscreen, keyboard or mouse, as certain non-exclusive examples. Alternatively, the term manually input can include any other manner and/or method that allows the operator or user to input information into the catheter system 210. In certain embodiments, the GUI 224 has been configured to allow the operator or user to manually input information relating to the fluid container 216. For example, the operator or user can manually input the tare weight, container dimension information and/or container weight information. Alternatively, the GUI 224 can also allow the operator or user to manually input a barcode, a model number, a radio frequency identification tag and/or any other form of an identification number (also sometimes collectively referred to as "identification information"). The identification information can generally be found on the fluid container 216. In various embodiments, the container measurement system 226 can be configured to determine the fluid quantity within the fluid container 216 by processing at least one of the tare weight, container dimension information, container weight information and/or identification information manually input by the operator or user with the GUI 224.

In other embodiments, the container measurement system 226 can also be configured to determine the fluid quantity within the fluid container 216 by processing container dimension information and/or container weight information received from the scale assembly 230. The design of the scale assembly 230 can vary. In the embodiment illustrated in FIG. 2, the scale assembly 230 can include a container scale 234 and a container sensor 236. The scale assembly 230 can include additional components or fewer components than those specifically illustrated and described herein.

The container scale 234 can measure and/or calculate container weight information. The design of the container scale 234 can vary. For example, the container scale 234 may have any suitable configuration, shape or size. The container scale 234 can include any suitable design that allows the container scale 234 to effectively measure and/or calculate container weight information. In one alternative embodiment, the container scale 234 can measure container dimension information by including a plurality of circular rings of varying diameter on which the fluid container 216 may be placed to determine the circumference and/or diameter of the fluid container 216.

The container sensor 236 can transmit or send electronic and/or other signals, e.g., sensor output, to the controller 232. In other words, the container sensor 236 can generate sensor output. The design of the container sensor 236 can vary. In some embodiments, the container sensor 236 can sense and/or measure container dimension information, and transmit or send sensor output relating to container dimension information to the controller 232. The container sensor 236 can sense container dimension information via any suitable manner and/or method. For example, in one embodiment, the container sensor 236 can sense container dimension information as the fluid container 216 is placed on or adjacent to the container scale 234. In another embodiment, the container sensor 236 can sense container dimension information, container weight information and/or the tare weight by recognition of identification information of the fluid container 216. In yet other embodiments, the container sensor 236 can transmit or send sensor output relating to container weight information to the controller 232. For example, in one embodiment, the container sensor 236 can transmit or send container weight information as the fluid container 216 is placed on or adjacent to the container scale 234.

In the embodiment illustrated in FIG. 2, the container sensor 236 can be integrated and/or included as part of the container scale 234. In other embodiments, the container sensor 236 may not be integrated or included as part of the container scale 234, but can be electrically connected and/or coupled to the container scale 234. Further, in certain embodiments, the container scale 234, the container sensor 236, or both, can be electrically connected and/or coupled to the controller 232.

The controller 232 is configured to receive and/or process container weight information from the container scale 234 and/or the sensor output transmitted or sent from the container sensor 236. The design of the controller 232 can vary. In various embodiments, based at least in part on the container weight information received from the container scale 234 and/or the sensor output received from the container sensor 236, i.e., related to container dimension information, the controller 232 can process container dimension information and/or container weight information provided by the container scale 234, the container sensor 236, or both, to determine the tare weight of the fluid container 216. The controller 232 can process container dimension information and/or container weight information to determine the tare weight of the fluid container 216 via any suitable manner and/or method. The controller 232 can further process the tare weight, container dimension information and/or container weight information to determine the fluid quantity within the fluid container 216. The controller 232 can process the tare weight, container dimension information and/or container weight information to determine the fluid quantity within the fluid container 216 via any suitable manner and/or method.

In alternative embodiments, the controller 232 can automatically detect and/or recognize the container capacity of the fluid container 216 by recognition of identification information and/or by processing the tare weight and container weight information. In one embodiment, the controller 232 can use an algorithm to eliminate and/or exclude fluid container(s) 216 by processing the tare weight and container weight information. For example, if fluid container(s) 216 having container weight information of 25 lbs (e.g., maximum amount of cryogenic fluid 228 to be contained within fluid container 216 of 15 lbs and tare weight of 10 lbs) and other fluid container(s) 216 having container weight information of 15 lbs (e.g., maximum amount of cryogenic fluid 228 to be contained within fluid container 216 of 10 lbs and tare weight of 5 lbs), if the container measurement system 226 measures container weight information of 20 lbs, the controller 232 can automatically detect and/or recognize that the fluid container 216 has the container capacity of 15 lbs.

Further, although shown in the embodiment illustrated in FIG. 2 as a separate structure, the controller 232 can be included as part of the control system 214. In other embodiments, the controller 232 can be separate from the control system 214.

In certain embodiments, the controller 232 can be electrically connected to the GUI 224. In such embodiments, the controller 232 can receive information manually input by the operator or user to determine the tare weight of the fluid container 216. For example, the controller can receive the tare weight, container dimension information, container weight information and/or identification information, manually input by the operator or user. The controller 232 can then process the tare weight, container dimension information, container weight information and/or identification information, to determine the fluid quantity within the fluid container 216 via any suitable manner and/or method. As one non-exclusive example, the controller 232 can use an algorithm to process at least one of the tare weight and/or container weight information to determine the fluid quantity. As another nonexclusive example, the controller can subtract the tare weight of the fluid container 216 from the weight of the fluid container 216 and cryogenic fluid 28 therein.

Additionally, the GUI 224 can provide the fluid quantity from the controller 232 to the operator or user. The GUI 224 can provide the fluid quantity to the operator or user visually by displaying picture, data, numbers or percentages, as non-exclusive examples. In certain non-exclusive embodiments, the GUI 224 can provide the operator or user with one or more of the following: a percentage of the fluid container 216 containing or not containing the cryogenic fluid 228, the fluid quantity contained within the fluid container 216, a volume of cryogenic fluid 228 contained within the fluid container 216 or a weight of cryogenic fluid 228 contained within the fluid container 216. However, any other suitable manner can be used by the GUI 224 to effectively provide and/or notify the operator or user of the fluid quantity.

Figure 3:
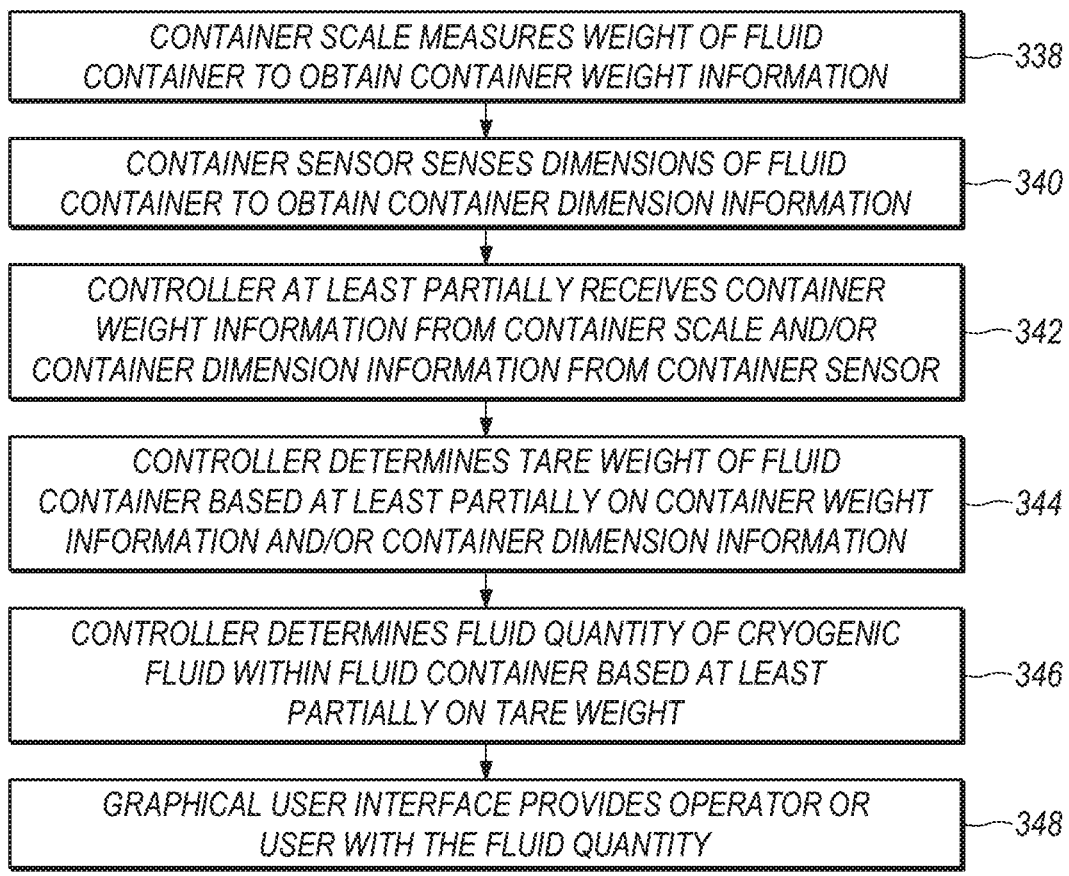
FIG. 3 is a flowchart outlining one embodiment of the operation of the fluid container measurement system.

FIG. 3 is a flowchart illustrating one embodiment of the operation of the container measurement system 326. It is appreciated that the order of the steps illustrated and described in FIG. 3 is not necessarily indicative of how the container measurement system 326 operates chronologically, as one or more of the steps can be combined, reordered, and/or performed simultaneously without deviating from the intended breadth and scope of the container measurement system and method.

At step 338, the container scale measures and/or calculates the weight of the fluid container to obtain container weight information. The container scale can obtain container weight information as the operator or user places the fluid container on the container scale.

At step 340, the container sensor senses dimensions of the fluid container to obtain container dimension information. The container sensor can sense container dimension information as the fluid container is placed on the container scale and/or by recognition of identification information of the fluid container.

At step 342, the controller at least partially receives container weight information from the container scale and container dimension information from the container sensor. The controller can process at least a portion of the container dimension information and/or the container weight information received from the container scale, the container sensor, or both.

At step 344, the controller determines the tare weight of the fluid container based at least in part on the container dimension information and/or the container weight information received from the container scale, the container sensor, or both.

At step 346, the controller determines the fluid quantity within the fluid container based at least in part on the tare weight.

At step 348, the GUI provides the operator or user with the fluid quantity. The GUI can provide the fluid quantity in various forms, e.g., displaying visually by picture, data, numbers, percentages, as non-exclusive examples. Once it has been determined that there is sufficient cryogenic fluid within the fluid container for the cryoablation procedure, the fluid container is ready for use during the cryoablation procedure. It is understood that these steps can be repeated as necessary to confirm that there is sufficient cryogenic fluid within the fluid container to successfully complete the cryoablation procedure.

Figure 4:
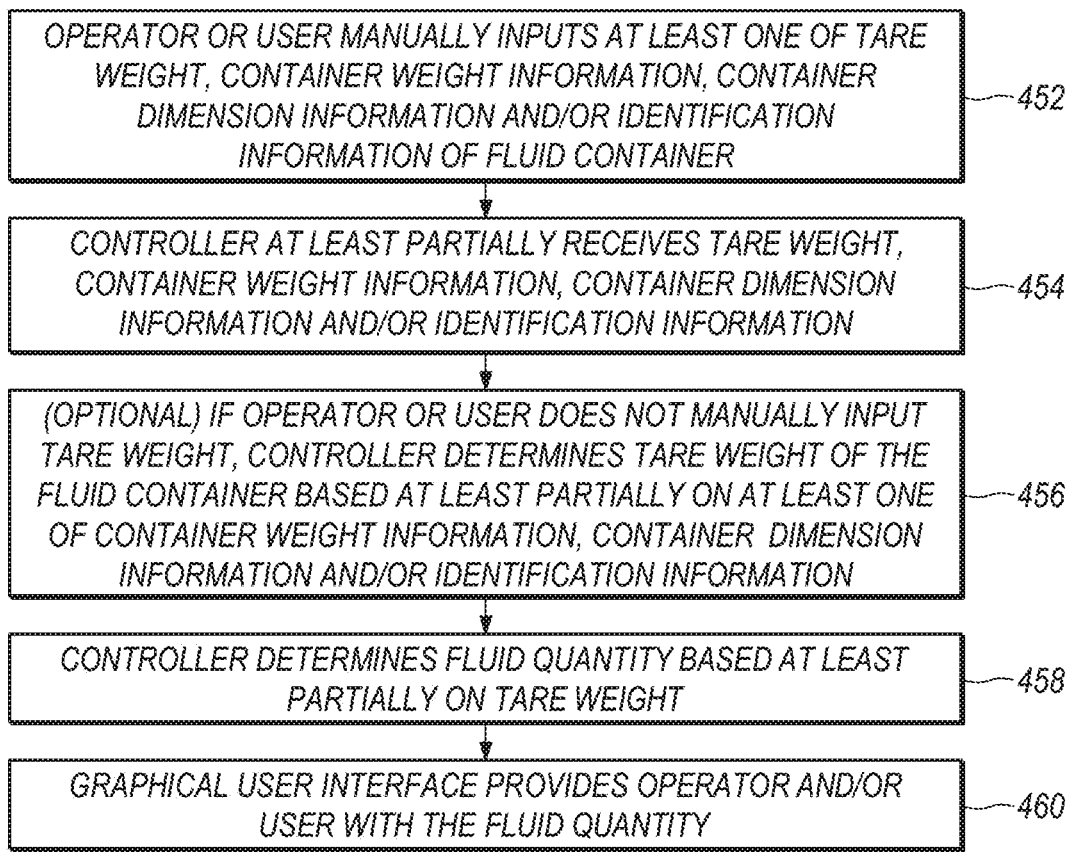
FIG. 4 is a flowchart outlining another embodiment of the operation of the fluid container measurement system.

FIG. 4 is a flowchart illustrating another embodiment of the operation of the container measurement system 426. It is appreciated that the order of the steps illustrated and described in FIG. 4 is not necessarily indicative of how the container measurement system 426 operates chronologically, as one or more of the steps can be combined, reordered, and/or performed simultaneously without deviating from the intended breadth and scope of the container measurement system 426 and method.

At step 452, the operator or user manually inputs with the GUI at least one of the tare weight, container dimension information, container weight information and/or identification information of the fluid container into the catheter system. The GUI has been configured to allow the operator or user to manually input the tare weight, container dimension information, container weight information and/or identification information for the controller to process.

At step 454, the controller at least partially receives the container dimension information, the container weight information, the identification information and/or the tare weight manually input with the GUI into the catheter system. The GUI may be connected and/or coupled to any one of the controller, the container scale and/or the container sensor.

At optional step 456, if the operator or user manually input container dimension information, container weight information and/or identification information, the controller determines the tare weight of the fluid container. The controller determines the tare weight of the fluid container based at least in part on at least one of the container dimension information, the container weight information and/or the identification information.

At step 458, the controller determines the fluid quantity within the fluid container based at least in part on the tare weight of the fluid container, either manually input with the GUI or determined by the controller, based at least in part on one of the container dimension information, the container weight information and/or the identification information.

At step 460, the GUI provides the operator or user with the fluid quantity. The GUI can provide the fluid quantity in various forms, e.g., displaying visually by picture, data, numbers, percentages, as non-exclusive examples. Once it has been determined that there is sufficient cryogenic fluid within the fluid container for the cryoablation procedure, the fluid container is ready for use during the cryoablation procedure. It is understood that these steps can be repeated as necessary to confirm that there is sufficient cryogenic fluid within the fluid container to successfully complete the cryoablation procedure.

Figure 5:
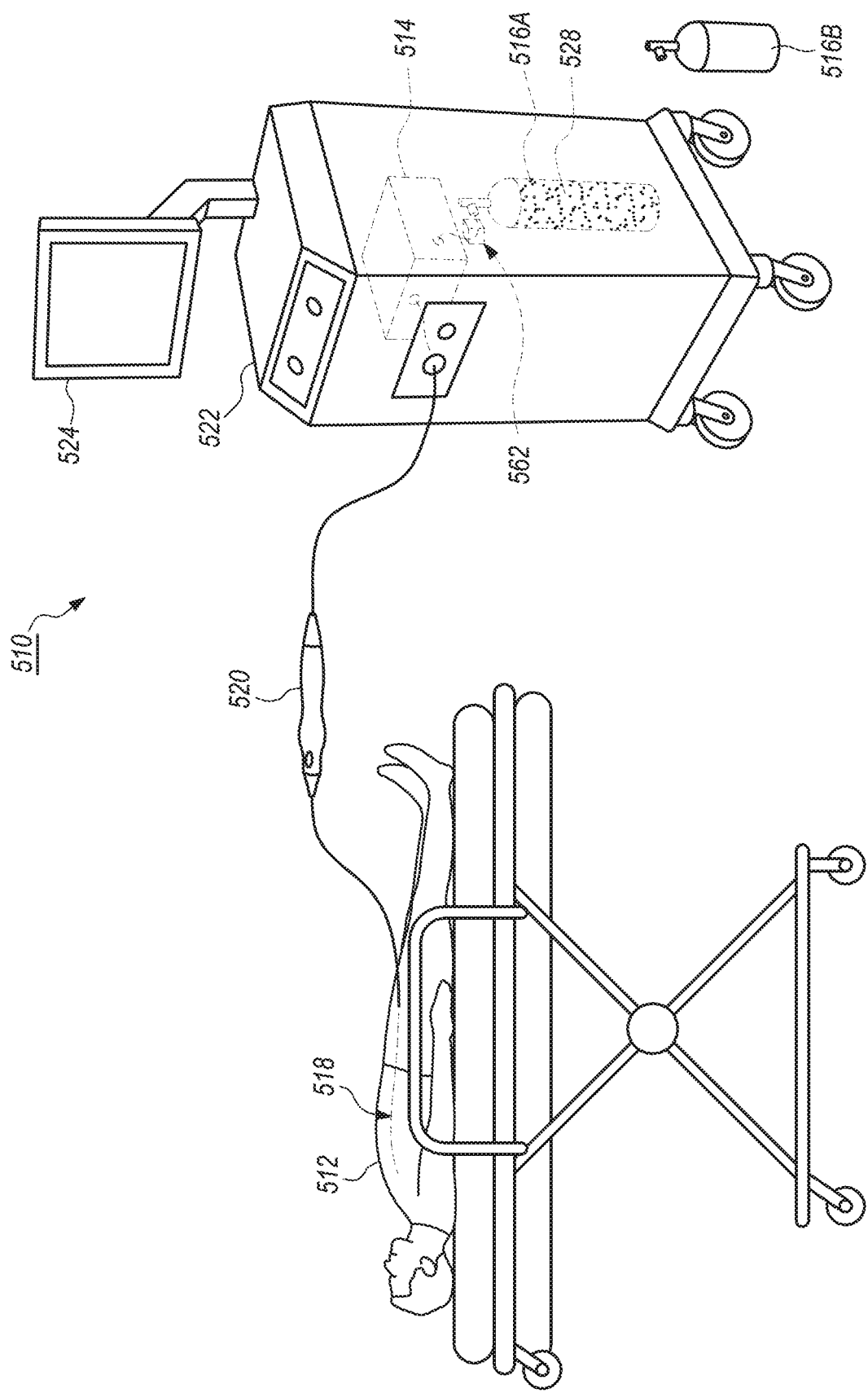
FIG. 5 is a schematic view of the patient, a replacement fluid container and another embodiment of the cryogenic balloon catheter system including a fluid container replacement system.

FIG. 5 is a schematic view of a patient 512, a replacement fluid container 516B, and another embodiment of the catheter system 510 including a container replacement system 562. In certain embodiments, such as the embodiment illustrated in FIG. 5, the catheter system 510 can include one or more of the control system 514, the fluid source 516, the balloon catheter 518, the handle assembly 520, the control console 522, the GUI 524 and the container replacement system 562. In this embodiment, the fluid source 516 can include one or more fluid container(s) 516A, 516B. For example, in some embodiments, the fluid source 516 can include fluid container(s) 516A and/or replacement fluid container(s) 516B. For ease of reference, the fluid container(s) 516A and the replacement fluid container(s) 516B may be referred to herein as "fluid container(s) 516." It is understood that although FIG. 5 illustrates the structures of the catheter system 510 in a particular position, sequence and/or order, these structures can be located in any suitably different position, sequence and/or order than that illustrated in FIG. 5.

The container replacement system 562 is configured to be more conveniently and safely utilized to replace the fluid container(s) 516A with the replacement fluid container 516B, e.g., when the level of the cryogenic fluid 528 within the fluid container(s) 516A falls below a certain specified or predetermined level. In particular, the container replacement system 562 is specifically configured to ensure that the fluid container 516A is fully and properly closed so that no cryogenic fluid 528 is able to escape during the replacement process, which may lead to injury for the operator or user. Once replaced, the replacement fluid container 516B can then be used for its intended purpose, e.g., to provide the necessary cryogenic fluid 528 for use by the catheter system 510.

In the embodiment illustrated in FIG. 5, at least a portion of the container replacement system 562 is positioned at a location within the control console 522. The container replacement system 562 can be positioned at any suitable location within the control console 522. Further, portions of the container replacement system 562 can be positioned partially within and/or outside the control console 522. Alternatively, the container replacement system 562 can be positioned at any suitable location outside of the control console 522. Additionally, and/or alternatively, the container replacement system 562 can be positioned at any other suitable location within the catheter system 510. In various embodiments, at least a portion of the container replacement system 562 can be electrically connected and/or coupled to the control system 514 and/or the GUI 524. The specific components and operations of the container replacement system 562 will be described in greater detail herein below in relation to the embodiments illustrated in FIGS. 6 and 7.

Figure 6:
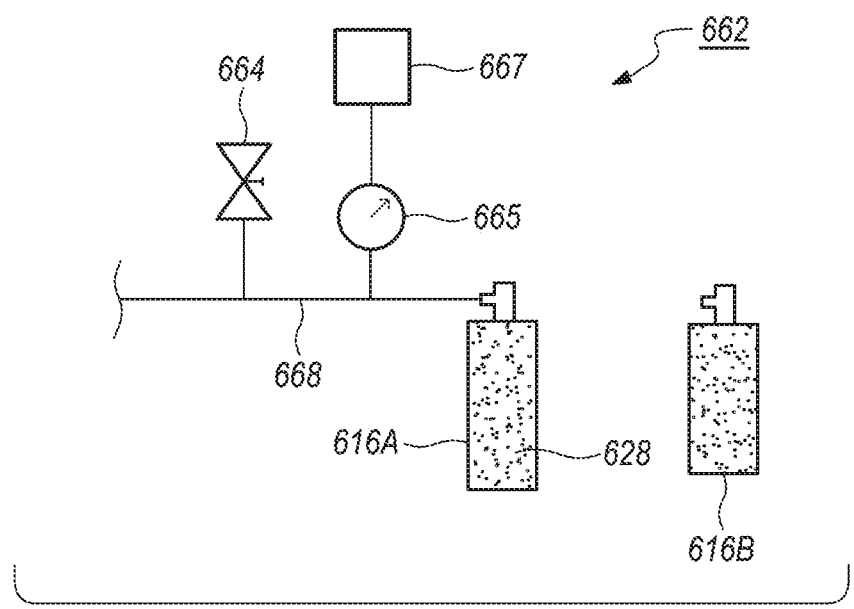
FIG. 6 is a simplified schematic side view of the replacement fluid container and one embodiment of the fluid container replacement system.

FIG. 6 is a simplified schematic side view of one embodiment of the container replacement system 662. The design of the container replacement system 662 can be varied. As shown in this embodiment, the container replacement system 662 includes one or more of a control valve 664, a pressure sensor 665 and a controller 667. Alternatively, the container replacement system 662 can include additional components or fewer components than those specifically illustrated and described herein. During use of the container replacement system 662, the container replacement system 662 is configured to verify if the fluid container 616A is fully and properly closed before notifying and/or instructing the operator or user or providing instructions to proceed with replacing the fluid container 616A with the replacement fluid container 616B.

The control valve 664 controls the venting of a pressure line 668 that leads from the fluid container 616A. The control valve 664 can include any suitable type of valve. The container replacement system 662 can be configured to open and close the control valve 664 to vent the pressure line 668 that leads from the fluid container 616A. When the control valve 664 is open, the pressure line 668 that leads from the fluid container 616A is actively being vented. In some embodiments, the control valve 664 can be manually controlled, i.e., opened or closed. In other embodiments, the container replacement system 662 can control the opening or closing of the control valve 664, such as via a controller 667, for example. The container replacement system 662 can control the control valve 664 via any suitable manner and/or method.

In the embodiment illustrated in FIG. 6, the control valve 664 is positioned on the pressure line 668. The control valve 664 can be positioned at any suitable location on the pressure line 668.

The pressure sensor 665 can measure and/or sense a line pressure, e.g., residual pressure, of any cryogenic fluid 628 within the pressure line 668. For example, after the control valve 664 is opened, the pressure sensor 665 can measure and/or sense the line pressure of any cryogenic fluid 628 remaining within the pressure line 668. In other words, after venting the pressure line 668, the pressure sensor 665 is utilized to measure and/or sense the line pressure of any cryogenic fluid 628 within the pressure line 668. Additionally, the pressure sensor 665 can transmit or send electronic and/or other signals, e.g., sensor output, to the controller 667. In other words, the pressure sensor can generate sensor output. As one non-exclusive example, sensor output can include the line pressure of the cryogenic fluid 628 within the pressure line 668. Alternatively, sensor output can include any other measurement related to pressure and/or line pressure within the pressure line 668.

In the embodiment illustrated in FIG. 6, the pressure sensor 665 can be positioned on the pressure line 668 between the control valve 664 and the fluid container 616A. Alternatively, the pressure sensor 665 may be positioned at any other location on the pressure line 668 that would enable the pressure sensor 665 to measure and/or sense the line pressure. Additionally, the pressure sensor 665 can be electrically connected and/or coupled to the controller 667.

The controller 667 is configured to receive and/or process the sensor output transmitted or sent from the pressure sensor 665. The design of the controller 667 can vary. The sensor output sensed and transmitted by the pressure sensor 665 can then be processed by the controller 667 to determine whether to replace the fluid container 616A with the replacement fluid container 616B. In one embodiment, the controller 667 can compare the line pressure of the cryogenic fluid 628 within the pressure line to a certain specified or predetermined line pressure (sometimes referred to herein as "threshold line pressure"). As used herein, the threshold line pressure can include any suitable pressure as determined by the operator or user that would enable the fluid container 616A to be safely replaced and/or exchanged. In some embodiments, "sensor output" may also include the threshold line pressure. For example, if the line pressure is sufficiently low, i.e., if the line pressure of the cryogenic fluid 628 within the pressure line 668 is below the threshold line pressure, then the controller 667 can determine that it is safe to proceed with replacing the fluid container 616A. In other words, the controller 667 can determine that replacing the fluid container 616A with the replacement fluid container 616B is permissible. Conversely, if the line pressure of the cryogenic fluid 628 within the pressure line 668 is not sufficiently low, i.e., if the line pressure is above the threshold line pressure, then the controller 667 can determine to more properly and completely close the fluid container 616A. In other words, the controller 667 can determine that replacing the fluid container 616A with the replacement fluid container 616B is not permissible. The controller 667 can process the sensor output via any suitable method. In one embodiment, the controller 667 can process the sensor output by use of algorithm. In another embodiment, the controller 667 can process the sensor output based at least in part on the threshold line pressure.

Further, although shown in the embodiment illustrated in FIG. 6 as a separate structure, the controller 667 can be included as part of the control system 514 (illustrated in FIG. 5). In other embodiments, the controller 667 can be separate from the control system 514. Additionally, and/or alternatively, the controller 667 can be integrated and/or included as part of any structure within the catheter system 510 (illustrated in FIG. 5).

Figure 7:
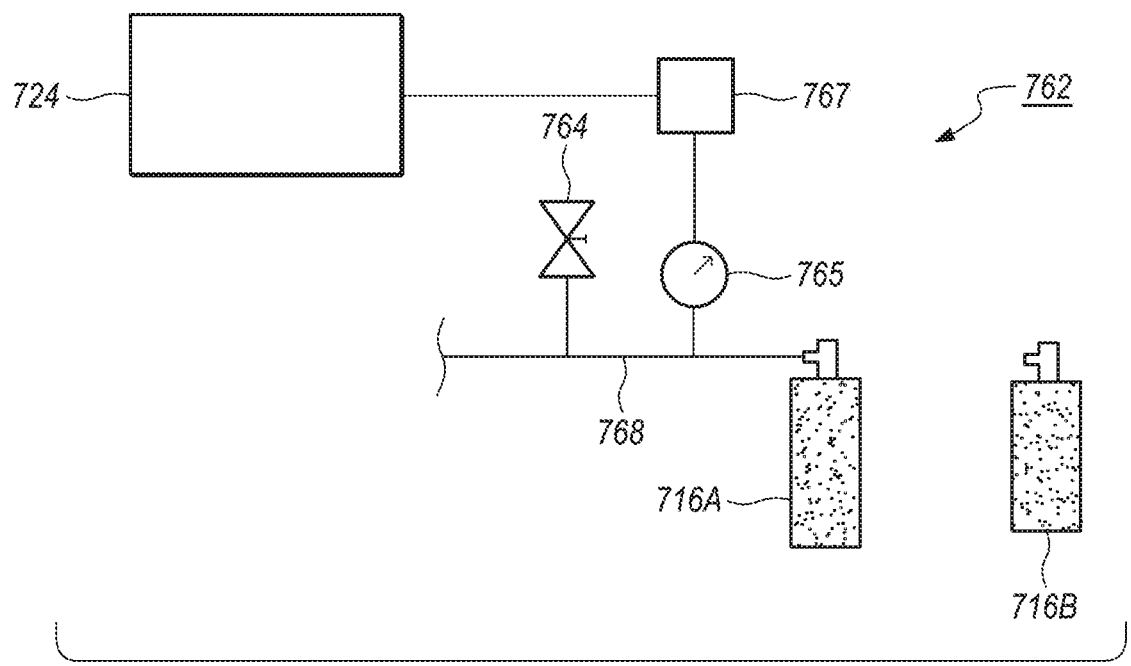
FIG. 7 is a simplified schematic side view of the replacement fluid container and another embodiment of the fluid container replacement system.

FIG. 7 is a simplified schematic side view of another embodiment of the container replacement system 762. In the embodiment illustrated in FIG. 7, the container replacement system 762 includes the GUI 724, the control valve 764, the pressure sensor 765 and the controller 767. In this embodiment, the GUI 724 is configured to act as an interface that enables the operator or user to interact with the fluid container 716A in a safe manner. More particularly, after the controller 767 has processed the sensor output to determine whether the fluid container 716A can be replaced, the GUI 724 can notify and/or instruct the operator or user whether replacing the fluid container 716A is permissible. In one embodiment, the GUI 724 can instruct the operator or user that replacing the fluid container 716A is permissible, i.e., that the fluid container 716A is fully and properly closed so that no cryogenic fluid 728 is able to escape during the replacement process. In another embodiment, the GUI 724 can instruct the operator or user that replacing the fluid container 716A is not permissible, i.e., that the fluid container 716A is not fully and properly closed. In such embodiment, the GUI 724 can instruct the operator or user to more fully and properly close the fluid container 716A. In other embodiments, the GUI 724 can provide a set of step-by-step instructions to guide the operator or user through the process of safely replacing or exchanging the fluid container 716A with the replacement fluid container 716B. The GUI 724 can provide the operator or user with the set of step-by-step instructions via any suitable manner and/or method. Additionally, it is understood that the set of step-by-step instructions can vary depending on the line pressure of the cryogenic fluid 728.

For example, if the line pressure is sufficiently low, i.e., if the line pressure of the cryogenic fluid 728 within the pressure line 768 is below the threshold line pressure, then the container replacement system 762, e.g., the GUI 724, can instruct the operator or user that it is safe to proceed with replacing the fluid container 716A. Conversely, if the line pressure of the cryogenic fluid 728 within the pressure line 768 is not sufficiently low, i.e., if the line pressure is above the threshold line pressure, then the GUI 724 can instruct the operator or user to more properly and completely close the fluid container 716A.

This general process can be repeated as necessary until the container replacement system 762 confirms that the line pressure within the pressure line 768 is sufficiently low, i.e., with the fluid container 716A being substantially if not completely closed, and it is an appropriate time to replace the fluid container 716A. At which point, in various embodiments, the GUI 724 can also provide the operator or user with the set of step-by-step instructions to guide the operator or user through the process of safely replacing or exchanging the fluid container 716A with the replacement fluid container 716B.

Figure 8:
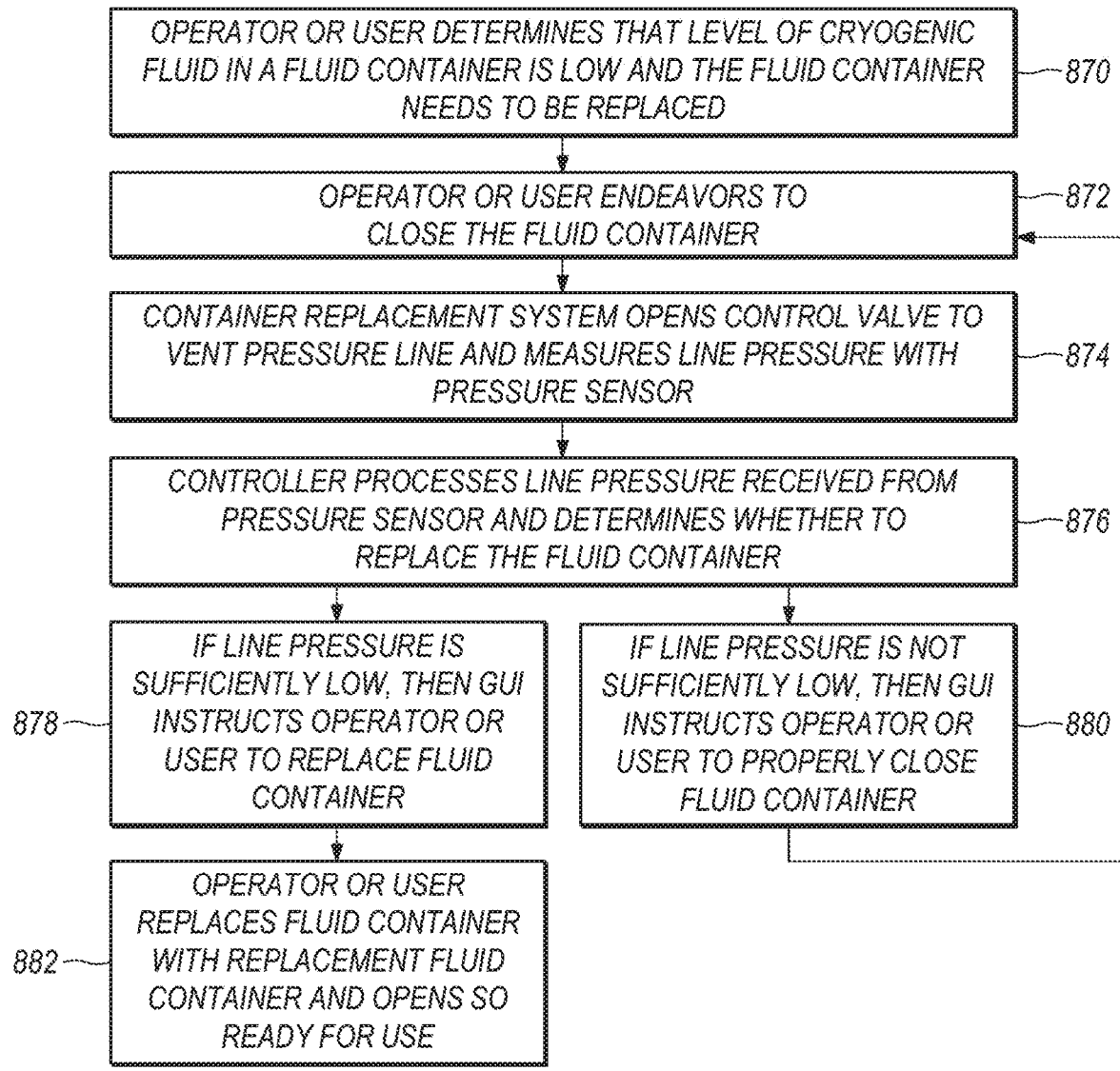
FIG. 8 is a flowchart outlining one embodiment of the operation of the fluid container replacement system.

FIG. 8 is a flowchart illustrating one embodiment of the operation of the container replacement system 862. It is appreciated that the order of the steps illustrated and described in FIG. 8 is not necessarily indicative of how the container replacement system 862 operates chronologically, as one or more of the steps can be combined, reordered, and/or performed simultaneously without deviating from the intended breadth and scope of the container replacement system 862 and method.

At step 870, the operator or user ascertains a quantity of the cryogenic fluid within the fluid container and determines whether the quantity of the cryogenic fluid is sufficiently low that it is a proper time to replace the fluid container. In certain embodiments, the quantity of the cryogenic fluid can be determined by use of a scale to ascertain the mass of cryogenic fluid within the fluid container. However, any other suitable manner of determining the quantity of the cryogenic fluid can be used. If the quantity of the cryogenic fluid within the fluid container is still sufficient for continued use, then the operator or user can continue to use the fluid container for additional cryoablation procedures. However, if the quantity of the cryogenic fluid within the fluid container is sufficiently low, the operator or user then understands that it is an appropriate time to replace the fluid container.

At step 872, the operator or user endeavors to close the fluid container.

At step 874, the container replacement system institutes the opening of the control valve to vent the pressure line and the subsequent measuring of the line pressure within the pressure line with the pressure sensor. In some embodiments, the control valve may be opened manually by the operator or user.

At step 876, the controller processes the line pressure received from the pressure sensor and determines whether to replace the fluid container with the replacement fluid container.

At step 878, if the line pressure within the pressure line is sufficiently low, i.e., below the threshold line pressure, then the GUI instructs the operator or user that it is an appropriate time to remove the fluid container and replace the fluid container with the replacement fluid container.

At step 880, if the line pressure within the pressure line is not sufficiently low, i.e., the line pressure is above the threshold line pressure, then the GUI instructs the operator or user to more fully and properly close the fluid container. The operator or user then returns to step 872, and again endeavors to close the fluid container. Once the operator or user has again endeavored to close the fluid container, the process then again continues through to step 878 where the container replacement system again checks to ensure that the fluid container is fully closed. It is understood that these steps can be repeated as necessary until the container replacement system confirms that the fluid container has been fully and properly closed to inhibit operator or user injury.

At step 882, once it has been determined that the fluid container is fully and properly closed, the operator or user can then proceed with removing and replacing the fluid container with the replacement fluid container. The GUI can also provide the operator or user with the necessary and desired step-by-step instructions for removing the fluid container and replacing the fluid container with the replacement fluid container. At that point, the operator or user can then open the replacement fluid container so that it is ready for use, e.g., the catheter system is again ready for use.

It is understood that although a number of different embodiments of the container measurement and replacement system have been illustrated and described herein, one or more features of any one embodiment can be combined with one or more features of one or more of the other embodiments, provided that such combination satisfies the intent of the present invention.

While a number of exemplary aspects and embodiments of the container measurement and replacement system have been discussed above, those of skill in the art will recognize certain modifications, permutations, additions and subcombinations thereof. It is therefore intended that the following appended claims and claims hereafter introduced are interpreted to include all such modifications, permutations, additions and sub-combinations as are within their true spirit and scope.

I claim:

1. A cryogenic fluid supply system for a cryogenic balloon catheter system including a cryoballoon catheter, the cryogenic fluid supply system comprising:
   a cryogenic fluid container configured to contain a cryogenic fluid;
   a pressure line fluidly coupled to the cryogenic fluid container and adapted to be fluidly coupled to the cryoballoon catheter to selectively deliver the cryogenic fluid to the cryoballoon catheter from the cryogenic fluid container;
   a vent conduit in fluid communication with the pressure line, the vent conduit including an in-line control valve, the vent conduit configured to selectively vent the cryogenic fluid from the pressure line through the control valve;
   a pressure sensor configured to sense a line pressure of the cryogenic fluid within the pressure line and to generate a sensor output based thereon; and
   a controller configured to control the in-line control valve and to receive and process the sensor output to determine whether the pressure line is fluidly isolated from the cryogenic fluid container based on the sensor output after the in-line control valve has been activated to vent the cryogenic fluid within the pressure line.

2. The cryogenic fluid supply system of claim 1, wherein the controller is configured to compare the sensed line pressure of the cryogenic fluid within the pressure line to a threshold line pressure based on the sensor output.

3. The cryogenic fluid supply system of claim 2, wherein the controller is configured to determine that the pressure line is fluidly isolated from the cryogenic fluid container if the sensed line pressure of the cryogenic fluid within the pressure line is below the threshold line pressure.

4. The cryogenic fluid supply system of claim 2, wherein the controller is configured to determine that the pressure line is not fluidly isolated from the cryogenic fluid container if the sensed line pressure of the cryogenic fluid within the pressure line is above the threshold line pressure.

5. A cryogenic fluid supply system for a cryogenic balloon catheter system including a cryoballoon catheter, the cryogenic fluid supply system comprising:
- a cryogenic fluid container configured to contain a cryogenic fluid;
- a pressure line fluidly coupled to the cryogenic fluid container and adapted for coupling to the cryoballoon catheter, the pressure line configured to selectively deliver the cryogenic fluid to the cryoballoon catheter from the cryogenic fluid container;
- a vent conduit in fluid communication with the pressure line, the vent conduit including an in-line control valve, the vent conduit configured to selectively vent the cryogenic fluid from the pressure line through the control valve;
- a pressure sensor configured to sense a line pressure of the cryogenic fluid within the pressure line and to generate a sensor output based thereon;
- a graphical user interface (GUI); and
- a controller operatively connected to the GUI and configured to receive and process the sensor output and determine whether the cryogenic fluid container is closed based on the sensor output;
- wherein the GUI is configured to instruct a user, responsive to the determination by the controller whether the cryogenic fluid container is closed, as to whether replacing the fluid container with a replacement fluid container is permissible by determining based on the sensor output that the line pressure of the cryogenic fluid within the pressure line is below a threshold line pressure.

6. The cryogenic fluid supply system of claim 5 wherein the GUI is configured to instruct the user that replacement of the fluid container is not permissible responsive to a determination by the controller, based on the sensor output, that a sensed line pressure of the cryogenic fluid within the pressure line is above a threshold line pressure.

7. The cryogenic fluid supply system of claim 5, wherein the control valve is configured to be manually controlled.

8. The cryogenic fluid supply system of claim 5, wherein the control valve is controlled by the controller.

9. The cryogenic fluid supply system of claim 8, wherein the controller is configured to cause the pressure sensor to sense the line pressure of the cryogenic fluid within the pressure line after the control valve has vented the cryogenic fluid within the pressure line.

10. A method for replacing a cryogenic fluid container of a cryogenic fluid supply system for a cryogenic balloon catheter system including a cryoballoon catheter, the cryogenic fluid container being fluidly coupled to a pressure line configured to deliver cryogenic fluid from the cryogenic fluid container to the cryoballoon catheter, the method comprising:
- opening a control valve fluidly coupled to the pressure line so as to vent the cryogenic fluid contained therein;
- generating a pressure sensor output indicative of a sensed line pressure within the pressure line;
- receiving, by a controller, the pressure sensor output; and
- determining, by the controller based on the pressure sensor output, whether the cryogenic fluid container is closed based on the pressure sensor output, whether the cryogenic fluid container is closed includes comparing the sensed line pressure of the cryogenic fluid within the pressure line with a threshold line pressure; and
- replacing the cryogenic fluid container with a replacement fluid container.

11. The method of claim 10, wherein opening the control valve is performed manually by a user.

12. The method of claim 10, wherein opening the control valve is performed automatically by the controller.

13. The method of claim 12, wherein generating the pressure sensor output is performed after opening the control valve.

14. The method of claim 13, further comprising a graphical user interface (GUI) instructing a user, responsive to the determination by the controller whether the cryogenic fluid container is closed, as to whether replacing the fluid container with a replacement fluid container is permissible.

* * * * *